United States Patent [19]

Cano

[11] Patent Number: 5,237,995

[45] Date of Patent: Aug. 24, 1993

[54] CONCENTRIC ELECTRODE FOR USE IN DETECTING LOW LEVEL BIOELECTRIC SIGNALS

[75] Inventor: Gerald G. Cano, Pittsburgh, Pa.

[73] Assignee: Allegheny-Singer Research Institute, Pittsburgh, Pa.

[21] Appl. No.: 675,999

[22] Filed: Mar. 26, 1991

[51] Int. Cl.$^5$ .......................................... A61B 5/0402
[52] U.S. Cl. .................................................... 128/640
[58] Field of Search ............................... 128/639–641, 128/644, 798, 802, 803

[56] References Cited

U.S. PATENT DOCUMENTS

| | | | |
|---|---|---|---|
| 3,868,947 | 3/1975 | Holsinger | 128/639 |
| 4,082,087 | 4/1978 | Howson | 128/640 |
| 4,362,165 | 12/1982 | Carmon | 128/640 |
| 4,448,199 | 5/1984 | Schmid | 128/639 |
| 4,583,549 | 4/1986 | Manoli | 128/640 |
| 4,763,660 | 8/1988 | Kroll et al. | 128/798 |
| 4,955,381 | 9/1990 | Way et al. | 128/798 |

Primary Examiner—Lee S. Cohen
Attorney, Agent, or Firm—Webb, Burden, Ziesenheim & Webb

[57] ABSTRACT

The present invention is directed to an electrode for use in measuring low level signals amidst competing noise signals. The electrode includes an electrically non-conductive substrate having a closed loop of electrical conductive and adhesive material carried by the substrate which defines therein an open area on the substrate. A first electrically conductive terminal is embedded within the closed loop of electrically conductive and adhesive material. Within the open area is an inner mass of electrically conductive and adhesive material. The inner mass of electrically conductive and adhesive material is spaced from the closed loop. The electrode also includes a second electrically conductive terminal which is embedded with the inner mass of electrically conductive and adhesive material. The electrode includes a first contact device for making electrical contact with the first terminal and a second contact device for making electrical contact with the second terminal.

8 Claims, 3 Drawing Sheets

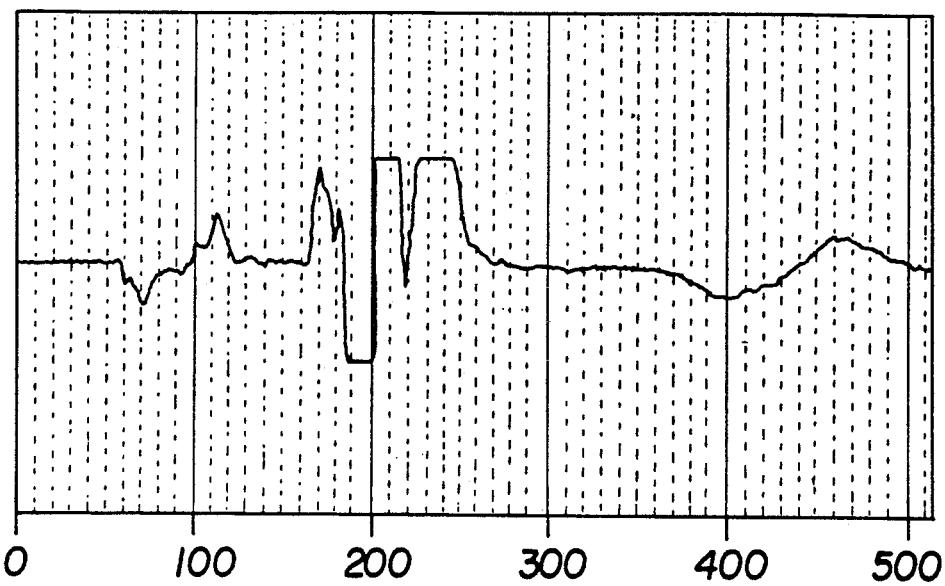
FIG._4A
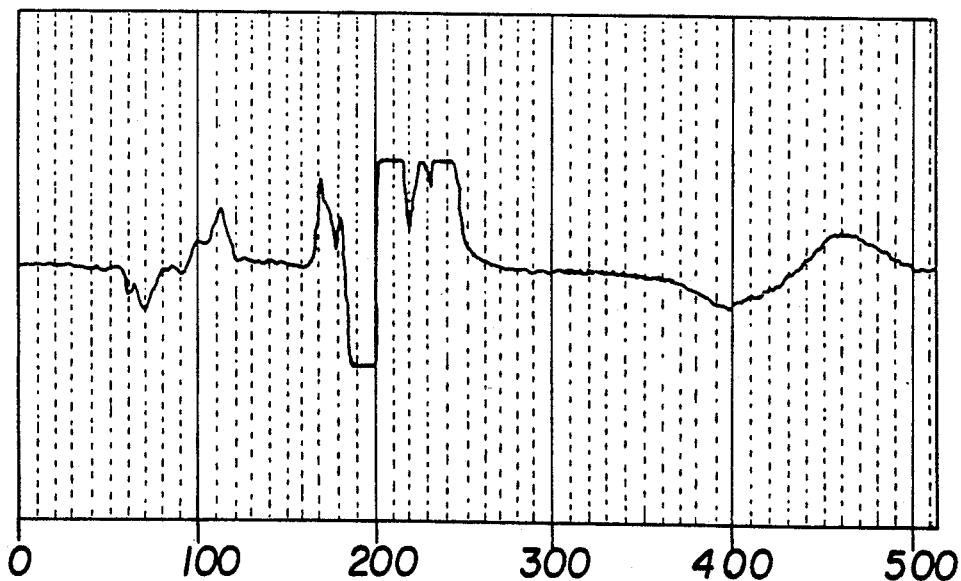
FIG._4B

CONCENTRIC ELECTRODE FOR USE IN DETECTING LOW LEVEL BIOELECTRIC SIGNALS

BACKGROUND OF THE INVENTION

1. Field of the Invention

This invention relates to electrodes used in detecting low amplitude bioelectric signals.

2. Description of the Prior Art

The detection of low level signals in the midst of competing noise signals is not easily accomplished, particularly with low level signals acquired at the surface of the body. Competing noise signals can obscure low amplitude signals which, if not obscured, could provide important information about a patient's condition. The detection and analysis of signals degraded by noise is a common problem that has been addressed in many ways.

Where the frequency components of the desired signal and the noise signals are distinctly separated, significant noise reduction can be accomplished with proper frequency filtering without altering the underlying desired signal. Where there is significant overlap between the frequency spectrum of the noise signal and the desired signal, separation of the desired signal from the noise signal is more difficult. This is a common problem in the analysis of biophysical signals. One common technique to enhance repetitive or cyclical signals is signal averaging of the time-domain signals. This results in one enhanced cycle of the desired signal. This problem has motivated development of other more sophisticated techniques, some of which seek to provide enhanced signal representation cycle-to-cycle or in very short-term averages.

These more sophisticated techniques often require at least two pairs of electrodes to acquire at least two signals for comparison. There are two constraints on the acquired signals. First, the underlying desired signals must be very similar. Second, the noise in the acquired signals must be very dissimilar, that is uncorrelated.

It has been found that when standard electrodes are utilized, the morphology of the acquired bioelectric signals, such as those found in the initial and terminal portions of the QRS complex of an electrocardiogram (ECG), can be significantly and undesirably different in each signal, particularly when acquisition amplifiers used in the acquisition of the signals have a very high gain. Thus, a need remains in the art for electrodes suitable for the acquisition of bioelectric signals with similar morphologies.

It is an object of the present invention to provide an improved electrode for the measurement of low level bioelectric signals on the surface of the body amidst competing noise signals, such that the signals acquired with the electrodes of the present invention will generate waveforms having similar morphology.

It is still another object of the present invention to provide an improved electrode for the measurement of ECGs on the surface of the body, wherein the signals acquired with the electrodes of the present invention will have a similar morphology in the initial and terminal portions of the QRS complex.

It is another object of the present invention to provide an improved electrode for the measurement of low level signals amidst competing noise signals.

It is still another object of the present invention to provide an improved concentric electrode which is quickly and easily attached to and removed from the surface of the body.

It is a further object of the present invention to provide an electrode which is inexpensive to construct and which is quickly and easily affixed to a given surface and is non-shorting.

SUMMARY OF THE INVENTION

Therefore I have invented an electrode for use in measuring low level signals amidst competing noise signals. The electrode includes an electrically non-conductive substrate having a closed loop of electrically conductive - and adhesive material carried by the substrate which defines therein an open area on the substrate. A first electrically conductive terminal is embedded within the closed loop of electrically conductive and adhesive material. Within the open area is an inner mass of electrically conductive and adhesive material. The inner mass of electrically conductive and adhesive material is spaced from the closed loop. The electrode also includes a second electrically conductive terminal which is embedded within the inner mass of electrically conductive and adhesive material. The electrode includes a first contact device for making electrical contact with the first terminal and a second contact device for making electrical contact with the second terminal.

The terminals of the electrode can rest directly on the substrate, or may be supported above the substrate by the electrically conductive and adhesive material.

In a preferred embodiment of the present invention, the electrically conductive material is a highly conductive solid electrode gel. Also, in one embodiment of the present invention, both terminals are made of metal. In a preferred embodiment of the present invention, the terminals are made of plastic and coated with silver-silver chloride.

BRIEF DESCRIPTION OF THE DRAWINGS

FIGS. 4A and 4B are graphs showing a pair of averaged ECGs computed from two different channels with concentric electrodes of the present invention.

DETAILED DESCRIPTION OF THE PREFERRED EMBODIMENTS

In the following discussion it is assumed that the electrode(s) are acquiring ECG signals, although it is to be understood that the present invention is in no way limited to ECG signals, but will work in any application requiring the detection of low level bioelectric signals obscured by competing noise signals.

Figure 1:
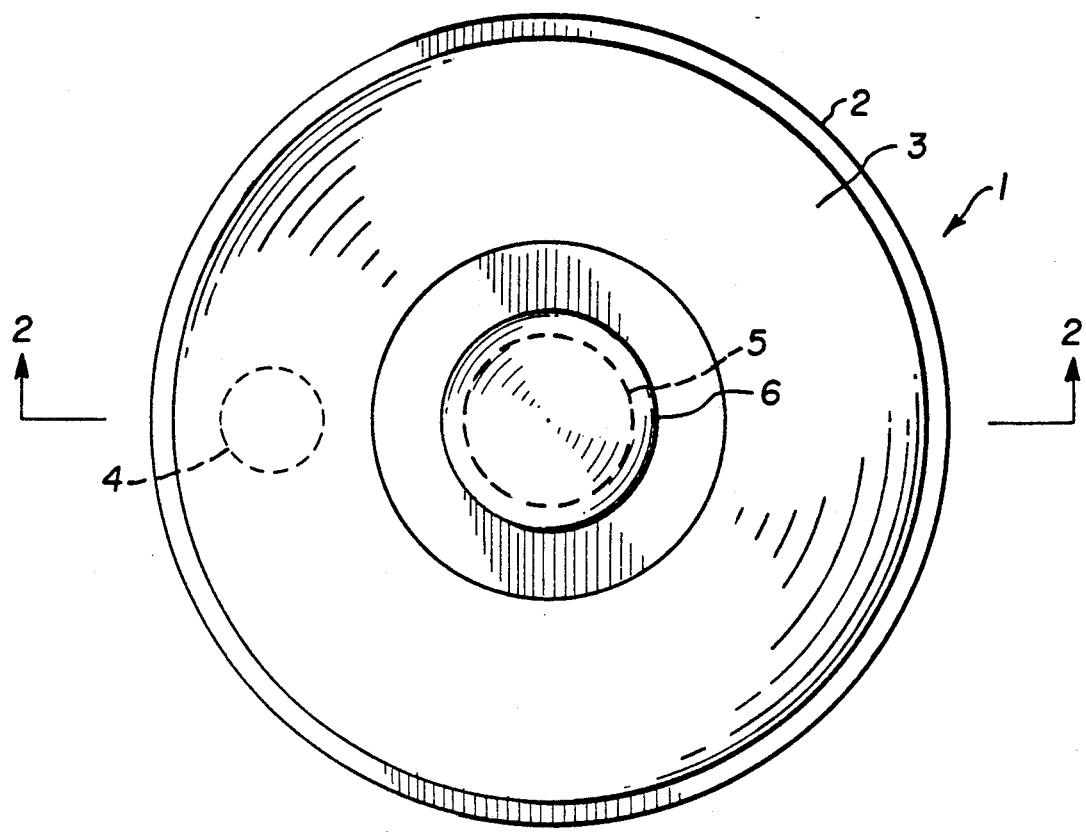
FIG. 1 is top plan view of a concentric electrode in accordance with the present invention.
Figure 2:
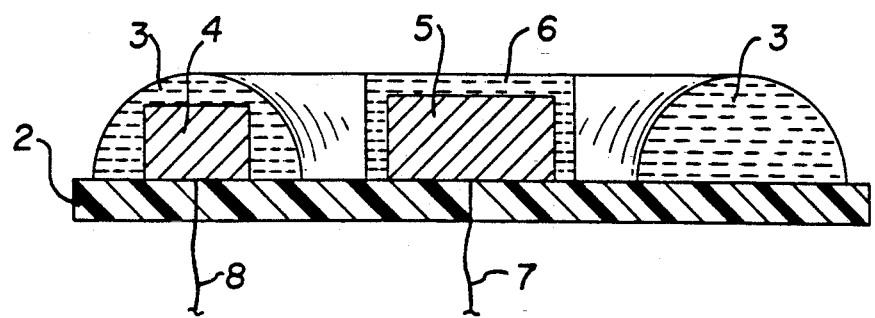
FIG. 2 is a section along the lines 2—2 of FIG. 1.

The construction of a concentric electrode 1 in accordance with the present invention is shown in FIGS. 1 and 2. The electrode 1 includes an electrically non-conductive substrate 2. Carried by the substrate 2 is a ring or closed loop 3 of electrically conductive and adhesive material. The loop 3 defines an open area therein on the substrate 2. Embedded in the loop 3 is a first electrically conductive terminal 4, shown in phantom in FIG. 1. The electrode 1 also includes an inner mass of electrically conductive and adhesive material 6 which is carried by the substrate 2. The mass 6 is within the open area bounded by the loop 3 and is both spaced and electrically discontinuous from the loop 3. A second electrically conductive terminal 5, shown in phantom in FIG. 1, is embedded within the mass 6. The electrode 1 includes a first contact device 8 for making electrical contact with the first terminal 4 and a second contact device 7 for making electrical contact with the second terminal 5. The contact devices 7, 8 are typically a lead, wire or strand-like conductive material.

The shape of the substrate 2 is not critical to the present invention and may take the form of a circular disk, square, regular or irregular geometric shape. The dimensions of the substrate 2 are also not critical to the present invention, however, for purposes of illustration, in one electrode I have made the substrate 2 a circular disk approximately 50 mm in diameter and 2 mm thick. Similarly, the material from which the substrate 2 is made is also not critical to the present invention, so long as it is electrically non-conductive. In a preferred embodiment, the substrate 2 is also flexible to facilitate attachment to the patient. Foam rubber or other flexible plastics are suitable materials for the substrate.

Similarly, the shape of the loop 3 of the present invention is not critical to the present invention, and may take the shape of a ring, square or any other regular or irregular geometric shape. It is only important that the loop 3 define an open area within the loop. Additionally, the loop 3 does not have to be centered on substrate 2, although this is a preferred embodiment. The material of which the loop 3 is made is not critical to the present invention, so long as it is highly conductive and will adhere the concentric electrode 1 of the present invention to a desired surface. In a preferred embodiment, the material is highly conductive and adhesive solid electrode gel. Any currently manufactured highly conductive and adhesive solid electrode gel is suitable for use with the present invention, such as the solid electrode gels used by Conmed Corporation in their standard ECG electrodes. Similarly, the dimensions of the loop 3, with respect to height and width are also not critical to the present invention, so long as the loop 3 is closed and sufficient surface area is presented which will effectively register the desired signals. In one electrode I have made as described above, the loop 3 is circular and is approximately 11 mm in width and approximately 0.5 mm in height.

The dimensions of the first terminal 4 are not critical to the present invention, nor is its exact shape. However, in one electrode I have made, the first terminal 4 is also a circular disk, approximately 10 mm in diameter and 0.5 mm in height. The first terminal 4 may be formed of any material provided at least on the surface is electrically conductive; a surface coating of metal is preferred. More preferred still is silver-silver chloride as a coating material on a plastic structure. The first terminal 4 can either rest directly on substrate 2 or it may be supported above the surface of substrate 2 by the electrically conductive and adhesive material of loop 3.

While the shape and dimensions of the second terminal 5 are not critical to the present invention, in one electrode I have made, where second terminal 5 is a circular disk, it is approximately 10 mm in diameter and 0.5 mm in height. The second terminal 5 can either rest directly on substrate 2 or it may be supported above the surface of substrate 2 by the electrically conductive and adhesive material of mass 6.

It is, however, preferred that the first and second terminals 4, 5 respectively, are constructed of the same material. Otherwise, different materials may exhibit different half-cell potentials, which will in turn create a voltage offset signal which places additional constraints on the signal acquisition electronics.

The exact dimensions of the mass 6 are not critical to the present invention, so long as the mass 6 is of a sufficient height to contact a given surface simultaneously with the loop 3. In one electrode I have made, where the second terminal 5 is a circular disk and is of the above described dimensions, the mass 6 is approximately 0.5 mm thick along the top of the second terminal 5 and is approximately 0.5 mm thick along the sides of the second terminal 5. While the mass 6 need not be centered within the open area of the substrate, a more or less centered mass 6 would be a preferred embodiment.

In applications where two electrodes are used to acquire signals, two differential signals are produced. One is the difference in potential between the two center electrodes obtained by connecting them to a signal receiving device, typically a differential amplifier. The second signal is the difference in potential between the outer electrodes obtained by connecting them to another signal receiving device, also typically a differential amplifier. Both amplifiers have the same gain. Such an arrangement of the concentric electrodes of the present invention allows for recording of ECG signals in general, on the surface of the thorax, and QRS activity in particular, of very similar morphology. This is particularly important in analysis of the terminal portion of the QRS complex.

FIGS. 3A, 3B, 4A and 4B illustrate the difference in signal morphology of the initial and terminal portions of an ECG waveform, and in the QRS complex in particular, of averaged ECGs computed from two different channels for 36 cycles utilizing standard electrodes versus the electrodes of the present invention. The horizontal axes of the graphs in FIGS. 3A, 3B, 4A and 4B provide milliseconds, the vertical axes provide the amplitude of the averaged signal. Amplifier gain and bandwidth for each of FIGS. 3A, 3B, 4A and 4B are 270,000 and 40 Hz to 400 Hz, respectively.

Figure 3A:
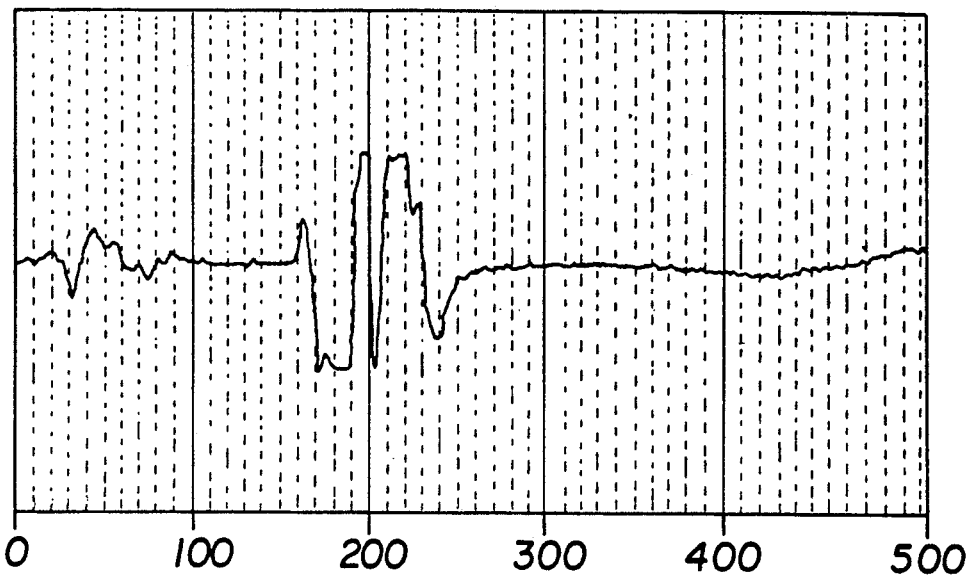
FIGS. 3A and 3B are graphs showing a pair of averaged ECGs computed with two different channels with standard electrodes.
Figure 3B:
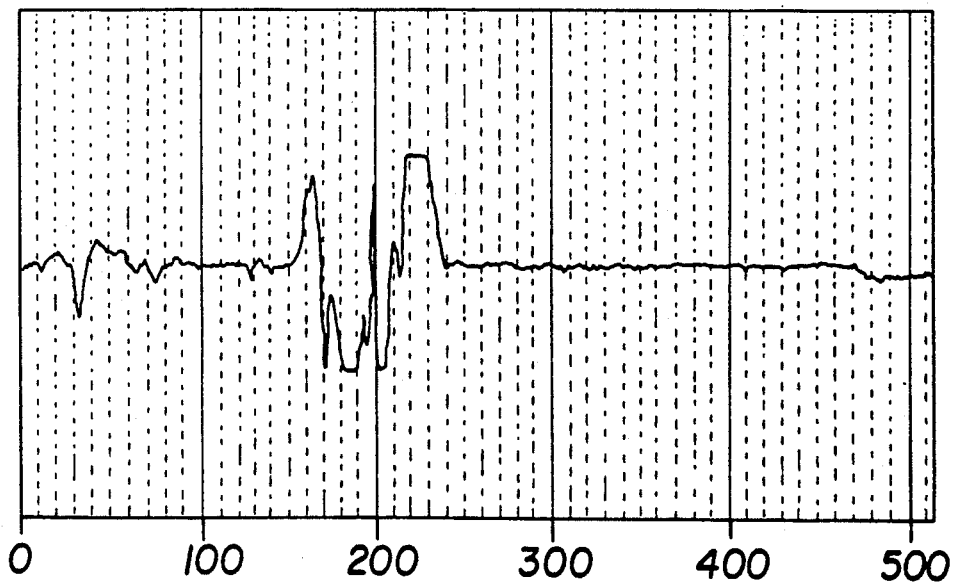

FIGS. 3A and 3B show that when standard electrodes are positioned on a patient, the ECG waveforms are different in the two channels. First, as shown at approximately 150 milliseconds, the amplitude of the deflection of the waveform in FIG. 3B is approximately 3 times greater than that of FIG. 3A. Additionally, at approximately 240 milliseconds, in the terminal portion of the QRS complex, there is a significant downward deflection in the waveform of FIG. 3A which is not at all present in FIG. 3B. Further, as a general pattern, the waveforms differ markedly from 260 to 400 milliseconds, where the waveform in FIG. 3A rises but does not do so in FIG. 3B, and in the trailing portions of 460 to 500 milliseconds where the waveform in FIG. 3A rises, unlike 3B for the same interval.

FIGS. 4A and 4B show that when concentric electrodes in accordance with the present invention are utilized, the signals obtained in FIGS. 4A and 4B show a high degree of similarity in morphology throughout the waveforms, but particularly in the initial and terminal portions of QRS complex.

While the present invention has been described with respect to the use of more than one electrode, a single electrode could also be used in certain applications. The difference in potential between the ring and the layer supplies the necessary potential difference to produce the signal, provided that the surface area of the inner layer and ring or closed loop are equal, otherwise there could be an impedance imbalance to the signal receiving device which could degrade the common mode capabilities of the signal receiving device.

Having described above the presently preferred embodiments of the present invention, it is to be understood that it may be otherwise embodied within the scope of the appended claims.

I claim:

1. An electrode particularly useful in acquiring low level signals on a surface, said electrode comprising:
   a) an electrically non-conductive substrate;
   b) a closed loop of electrically conductive and adhesive material carried by said substrate and defining therein an open area on said substrate;
   c) a first electrically conductive terminal embedded within said closed loop of electrically conductive and adhesive material;
   d) an inner mass of electrically conductive and adhesive material carried by said substrate within said open area and spaced from said closed loop;
   e) a second electrically conductive terminal embedded within said inner mass of electrically conductive and adhesive material;
   f) first contact means for making electrical contact with said first terminal; and
   g) second contact means for making electrical contact with said second terminal.

2. The electrode of claim 1 wherein said electrically conductive and adhesive material is a highly conductive solid electrode gel.

3. The electrode of claim 1 wherein said terminals are each formed of the same material.

4. The electrode of claim 1 wherein said terminals are each formed of metal.

5. The electrode of claim 1 wherein said terminals are each formed of silver-silver chloride.

6. The electrode of claim 1 wherein said terminals are supported by said substrate.

7. The electrode of claim 1 wherein said closed loop is a ring.

8. The electrode of claim 1 wherein said terminals are supported by said electrically conductive and adhesive material and are not in direct physical contact with said substrate.

* * * * *